US007654668B2

(12) United States Patent
Neuhann et al.

(10) Patent No.: US 7,654,668 B2
(45) Date of Patent: Feb. 2, 2010

(54) DEVICE AND METHOD FOR DETECTING THE SPATIAL POSITION OF THE OPTICAL AXIS OF AN EYE AND FOR CENTERING A REFERENCE SYSTEM RELATION TO THE OPTICAL AXIS

(76) Inventors: Thomas Neuhann, Herzogstrasse 48, 80801 München (DE); Jörg M. Hassel, Adalmuntstr. 32, 82284 Grafrath (DE)

( * ) Notice: Subject to any disclaimer, the term of this patent is extended or adjusted under 35 U.S.C. 154(b) by 68 days.

(21) Appl. No.: 11/571,178

(22) PCT Filed: Jun. 23, 2005

(86) PCT No.: PCT/EP2005/006824

§ 371 (c)(1),
(2), (4) Date: Dec. 6, 2007

(87) PCT Pub. No.: WO2006/000423

PCT Pub. Date: Jan. 5, 2006

(65) Prior Publication Data

US 2008/0204657 A1     Aug. 28, 2008

(30) Foreign Application Priority Data

Jun. 25, 2004     (DE) .................. 10 2004 030 904

(51) Int. Cl.
*A61B 3/10*     (2006.01)
*A61B 3/14*     (2006.01)
(52) U.S. Cl. ....................... 351/205; 351/208
(58) Field of Classification Search .......... 351/205–246
See application file for complete search history.

(56) References Cited

U.S. PATENT DOCUMENTS

| 4,373,787 | A |  | 2/1983 | Crane et al. |
| 4,443,075 | A |  | 4/1984 | Crane |
| 4,729,652 | A |  | 3/1988 | Effert |
| 5,270,748 | A |  | 12/1993 | Katz |
| 2002/0198516 | A1 |  | 12/2002 | Knopp et al. |
| 2006/0192921 | A1 | * | 8/2006 | Loesel et al. ................. 351/219 |

FOREIGN PATENT DOCUMENTS

| EP | 1 209 553 A1 | 5/2002 |
| WO | WO 01/4606 A | 6/2001 |

* cited by examiner

*Primary Examiner*—Mohammed Hasan
(74) *Attorney, Agent, or Firm*—Antonelli, Terry, Stout & Kraus, LLP.

(57) ABSTRACT

A method and a device for detecting the spatial position of the optical axis of the eye of a human or animal subject and for centering a reference system in relation to the optical axis are described, having at least one light source emitting a parallel light beam bundle, a positioning region for the subject provided opposite the light source, means for relative position orientation of the parallel light beam bundle in relation to the eye of the subject, and at least one detector unit for detecting reflection events caused in and on the eye by the parallel light beam bundle. The present invention generates control signals on the basis of the scattering and reflection events detected by the detector unit, by which the means for relative position orientation are activated, the control signals being generated in such a way that at least one reflection event and at least one scattered light event are to be brought into congruency in relation to the propagation direction of the parallel light beam bundle.

20 Claims, 4 Drawing Sheets

(12) United States Patent
US 7,654,668 B2

DEVICE AND METHOD FOR DETECTING THE SPATIAL POSITION OF THE OPTICAL AXIS OF AN EYE AND FOR CENTERING A REFERENCE SYSTEM RELATION TO THE OPTICAL AXIS

BACKGROUND OF THE INVENTION

1. Field of the Invention

The present invention relates to a device and a method for detecting the spatial position of the optical axis of the eye of a human or animal subject and for centering a reference system in relation to the optical axis, having at least one light source, which emits a parallel light beam bundle, a positioning region for the subject provided opposite the light source, means for relative position orientation of the parallel light beam bundle in relation to the eye of the subject, and at least one detector unit for detecting reflection events caused in and on the eye by the parallel light beam bundle.

2. Description of the Prior Art

Devices of the species described above are predominantly used in the field of ophthalmology, particularly for correcting the defective sight of an eye using a laser treatment system, particularly an excimer laser, to provide a targeted material removal on or inside the cornea, to achieve a desired change of the corneal curvature and a correction of the optical action of the cornea connected thereto.

The photorefractive correction of defective sight has been a recognized and very effective method for correcting vision errors for years. In the meantime, all types of defective sight such as nearsightedness (myopia), farsightedness (hyperopia), and corneal curvatures (astigmatism) have been treated very successfully using appropriately equipped laser systems. A requirement for successful treatment requires exact positioning of the treatment laser beam in relation to the cornea to be treated.

With increasing precision of the excimer laser systems and the precision of the diagnostic methods available, exact positioning of the treatment laser beam at the location of the cornea gains ever greater significance. A few years ago, the photorefractive correction of defective sight was modified by the simple use of the spectacle prescription as starting information in such a way that the spatially resolved aberrations of the entire system of the eye were measured using wavefront technology and the topographic properties of the cornea, and a corresponding correction guideline for the treatment laser beam was prepared.

It is a direct consequence that with the significant increase of detailed information available to the photorefractive correction, precise positioning of the eye to be treated and/or the treatment at the location of the cornea gains significance.

Treatment laser systems of this type are generally supported by eye tracker systems, which are based on greatly varying method technologies. With the aid of systems of this type, position changes of the eye in the magnitude of less than 100 μm may be recognized.

An essential requirement for successful correction of defective sight is thus precise orientation and positioning of the treatment laser beam in relation to the eye to be treated and its optical axis, and/or the optical axes of its refractive partial faces. The practice typical until now for adjusting a treatment laser beam in relation to the eye was performed up to this point in relation to the pupil center or purely subjectively by the treating physician, who oriented himself either on unchanging eye features or manually adjusted the treatment laser beam as a function of light reflections occurring on or in the eye. All laser-supported refractive surgery methods known up to this point for optimized correction of defective sight in the eye therefore lack an objectively repeatable adjustment of the treatment laser beam in relation to the eye to be treated and its optical axis, and/or the optical axes of its refractive partial faces.

SUMMARY OF THE INVENTION

The invention is a device and a method, which the treating physician uses when performing laser-supported photorefractive correction on an eye, and which may automatically adjust the treatment laser beam required for this purpose under exclusively objective framework conditions in relation to the eye. It is thus possible to implement an objective and exactly reproducible fixing of the optimum position of the treatment laser beam to perform the laser treatment on the cornea, which is independent of the operating precision of the particular operator.

The device according to the present invention allows the physician to orient the treatment laser beam on the basis of the individual optical axis of the eye to be treated and/or its refractive partial face to be treated, which may be determined automatically by the device according to the present invention.

For this purpose, the device for detecting the spatial position of the optical axis of the eye of the human or animal subject and for centering a reference system, preferably a treatment laser beam, in relation to the optical axis of the eye has the following components. It is noted here that the device is also usable on animals, but the further embodiments are restricted, without restricting the invention, exclusively to eye correction and/or determining the optical axis in the human eye. The components are:

- at least one light source, which emits a parallel light beam bundle, for which a laser emitting in the visible or near-infrared spectral range is preferably suitable, whose light wavelength is not to unfold any therapeutic effect on the eye;
- a positioning region for the subject, provided opposite the light source, so that the location of the eye to be treated assumes a largely spatially defined position. A head support adaptable to the head contour is preferably used for this purpose, in which the head of the subject may be laid spatially fixed;
- means for relative position orientation of the parallel light beam bundle in relation to the eye of the subject. In the simplest case, the means are a substrate implemented as an x/y positioning table, which is movable in a controlled way in at least one plane, which intersects the beam direction of the parallel light beam bundle perpendicularly, the positioning table may especially preferably also be moved in the beam direction, that is, in the z direction; and
- at least one detector unit for detecting reflection and scattered light events caused in and on the eye by the parallel light beam bundle. In principle, any type of light-sensitive detector system is suitable and preferably an imaging camera system, such as a video camera, is suitable for the detector unit.

The device is distinguished according to the present invention in that an analysis unit is provided, which generates control signals on the basis of the reflection and scattered light events detected by the detector unit, by which the means for relative location orientation are activated, the control signals being generated in such a way that at least one reflection event and at least one scattered light event are to be brought into congruency in relation to the propagation direction of the parallel light beam bundle.

The device according to the present invention, which makes it possible to automatically find at least one reflection event occurring in or on the eye and one scattered light event, determines the visual and/or optical axis of the eye to be treated and/or one or more of its refractive partial faces by bringing a reflection event occurring on or in the eye and a scattered light event into congruency. Subsequently, the treatment laser beam required for performing the photorefractive correction is oriented knowing the spatial position of the optical axis.

The eye of the subject is automatically moved in relation to the parallel light beam bundle to find and/or detect the optical axis and for a readjustment between the treatment laser beam and the optical axis which is required while performing a photorefractive correction, so that exact orientation between eye and light source and finally the reference system to be viewed as the treatment laser beam is ensured during the entire engagement. For this purpose, the control signals, which are used for activating a x-y adjustment table, on which the subject rests, corresponding to the reflection and/or scattered light events detected by the detector unit, are generated using computer-supported image processing. An adjustment table which is additionally movable in height, that is, in the z direction and/or along the beam direction of the parallel light beam bundle, is preferably suitable.

In principle, reflection and/or scattered light events result in or on the eye due to the parallel light beam bundle at interfaces inside the eye, at which two material layers having different indices of refraction meet.

Light beams are thus refracted and reflected on various surfaces of the eye. A first reflection of a light beam incident on the eye surface occurs at the surface of the cornea itself and is typically also referred to as a corneal reflection. The corneal reflection is also referred to in the literature as the first Purkinje image. The second, third, and forth Purkinje images arise at the interfaces of cornea/aqueous humor, aqueous humor/lens, and lens/vitreous humor of the eye, respectively.

In addition, when a parallel light beam bundle shines through the cornea of the eye as the first optical component of the eye, the cornea exerts an optical effect on the beam bundle comparable to that of a converging lens, which typically has a radius of curvature in the magnitude of approximately 7.4 mm. To find the optical axis of the eye, at least two light points lying on or in the eye, which are caused by the beam bundle, must be recognized and brought into congruency.

If the eye of the patient is illuminated using a parallel light beam bundle, the patient is to fixate on the punctual light source, from which the parallel light beam bundle originates, appearing optically to the patient to be treated as a punctual light source. Upon observation of the eye, the following light appearances and/or light points may be established as a result of reflection and scattering effects on and in the eye:

the fixation light source appearing as a scattered light event,
the fovea centralis of the retina, because of the fixation by the patient, and
the first Purkinje image of the fixed light source, which appears as a reflection event on the cornea surface.

If a fixation light source having a parallel light beam bundle is used, such as an LED, the passage point of the parallel light beam bundle through the cornea, which may be recognized from a weak scattered light reflection on the cornea surface, may be moved over a comparatively broad area of the cornea without the patient looking after the fixation light source, whose location is changing, since the patient thinks the patient sees the light source in infinity because of its parallel beam property and does not recognize the position displacement of the light source, which is actually located in the finite. If the passage point of the parallel light beam deviates further from the location of the optical axis of the eye, that is, if the passage point is eccentric, the scattered light reflection or the scattered light event of the fixation light source appears less bright the more eccentric the passage point.

To now find the penetration point of the parallel light beam through the cornea surface which lies exactly on the optical axis of the eye, the scattered light event on the cornea surface and, in addition, the first Purkinje image arising as a reflection event in the fixation light source—under the condition of central fixation by the patient—must be aligned, that is, lie along a shared spatial axis. This is precisely the case when the first Purkinje image coaxial with the fixation light beam causes a strong, that is, especially bright reflection phenomenon on the eye for the observer, that is, for the treating physician. In this constellation, the parallel light beam incident on the cornea surface at the location of the first Purkinje image is reflected back into itself and is additionally superimposed with the scattered light event of the fixation light source. It is obvious that a light point of maximum light intensity unmistakably results for the treating physician, which represents a unique navigation aid for determining the spatial position of the optical axis of the eye of the patient to be examined and treated.

This may be applied accordingly for other refractive partial faces of the eye to determine their position.

The configuration thus described offers a practically locationally fixed indication of the location at which the optical axis of the cornea "penetrates" its surface under the fixation condition on the basis of the properties discussed above. This penetration point, however, is the most suitable center for a change of curvature which alters refractive power, for example, with the aid of a laser.

On the basis of these properties, the detector unit of the device according to the present invention has at least one optical imaging system, by which the particular scattered light and reflection events occurring in the area of the air/cornea interface may be imaged sharply.

Through the optical detection of the first Purkinje image (reflection event) and the scattered light event on the detector unit, which is preferably implemented as a video camera, whose field of vision is directed at least on the pupil area of the eye and which, in addition, provides a location-resolving image plane for detecting the position of the reflection and scattered light events which may be imaged in the image plane of the camera, using a computer-supported image analysis unit, the distance and the relative positions between the corneal reflection and the scattered light event are ascertained. Moreover, the corneal reflection and the scattered light event are brought into congruency by targeted position change of the eye. A trajectory is calculated on the basis of the position and distance information obtained during the image analysis, along which the eye is to be moved to bring both light events into congruency and finally to be stopped in this position, at least until a photorefractive correction has been completed.

As already noted, this is performed by actively monitored regulated relative motion of the subject in relation to the parallel light beam bundle.

If the optical axis of the eye has been detected in the above way and correspondingly adjusted in relation to the parallel light beam bundle, a treatment laser beam may be coupled along the parallel light beam bundle to perform the photorefractive correction, which performs desired manipulations on the eye by targeted ablation or coagulation of tissue areas in or on the eye.

BRIEF DESCRIPTION OF THE DRAWINGS

The present invention is explained for exemplary purposes in the following with restriction of the general idea of the present invention on the basis of an exemplary embodiment with reference to the drawing.

DESCRIPTION OF THE INVENTION

Figure 1:
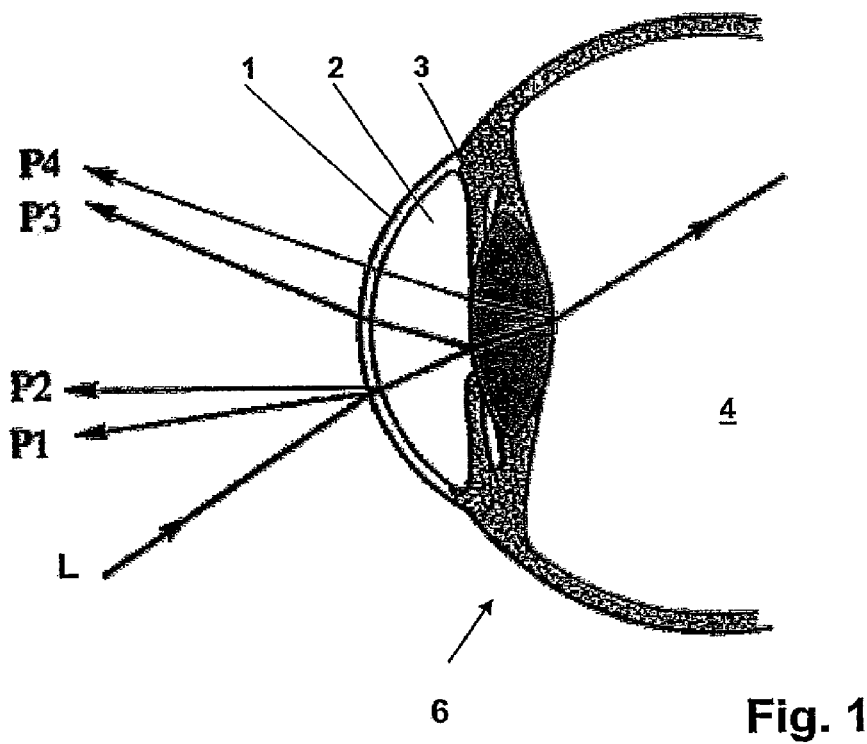
FIG. 1 shows an illustration of reflection events occurring on the eye.

FIG. 1 shows a schematic partial cross-section through a human eye 6, which has a cornea 1, aqueous humor 2, a lens 3, and the vitreous humor and/or eye inner chamber 4. If a light beam L is incident on the surface of the cornea 1, a part of the light beam is reflected at the interface air/cornea surface. The reflection event P1 in this regard is referred to as the Purkinje image P1 or as the corneal reflection. Similar reflection events P2-P4 occur at the interfaces of cornea 1/aqueous humor 2, aqueous humor 2/lens 3, and lens 3/vitreous humor 4.

Moreover, the reflection event P1 at the cornea surface and a scattered light event PS occurring in the course of the optical scattering at the cornea surface are used for ascertaining the visual axis A of the entire system, as described at the beginning.

Figure 4:
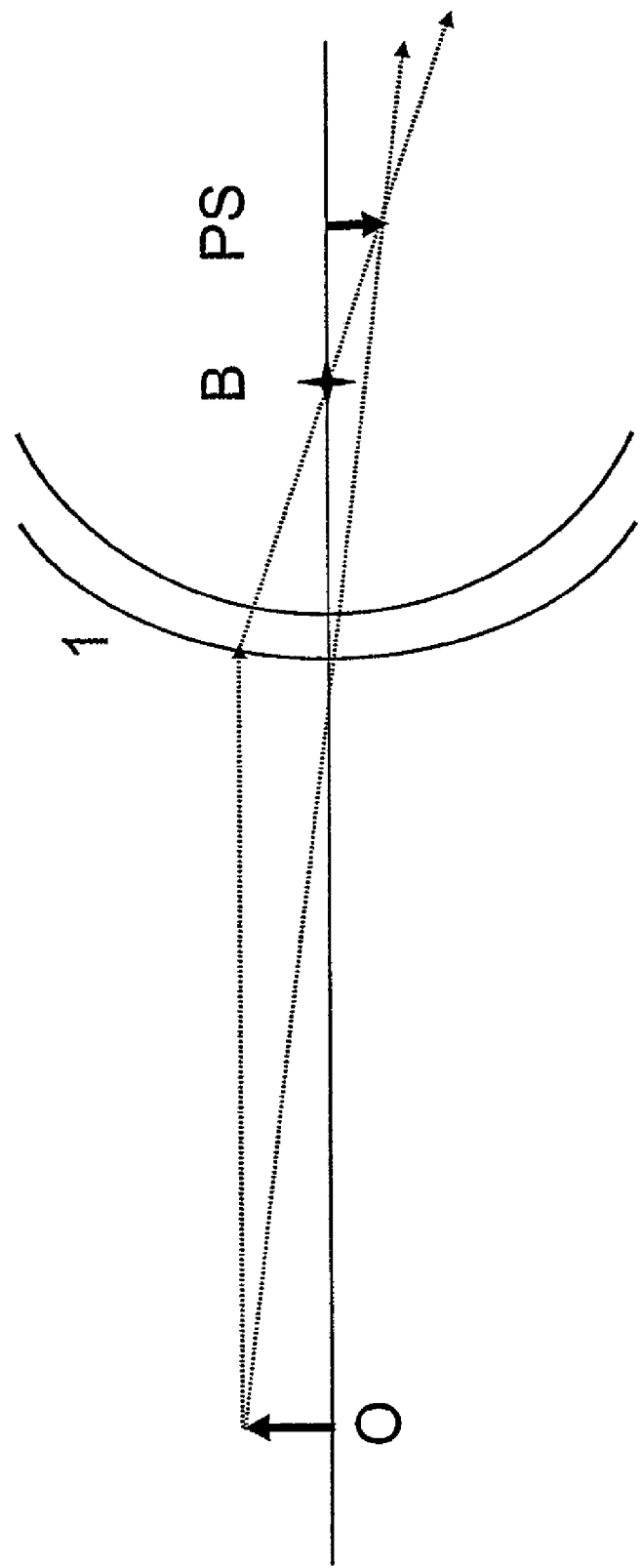
FIG. 4 shows beam geometry for the occurrence of a virtual image within an eye.
Figure 5:
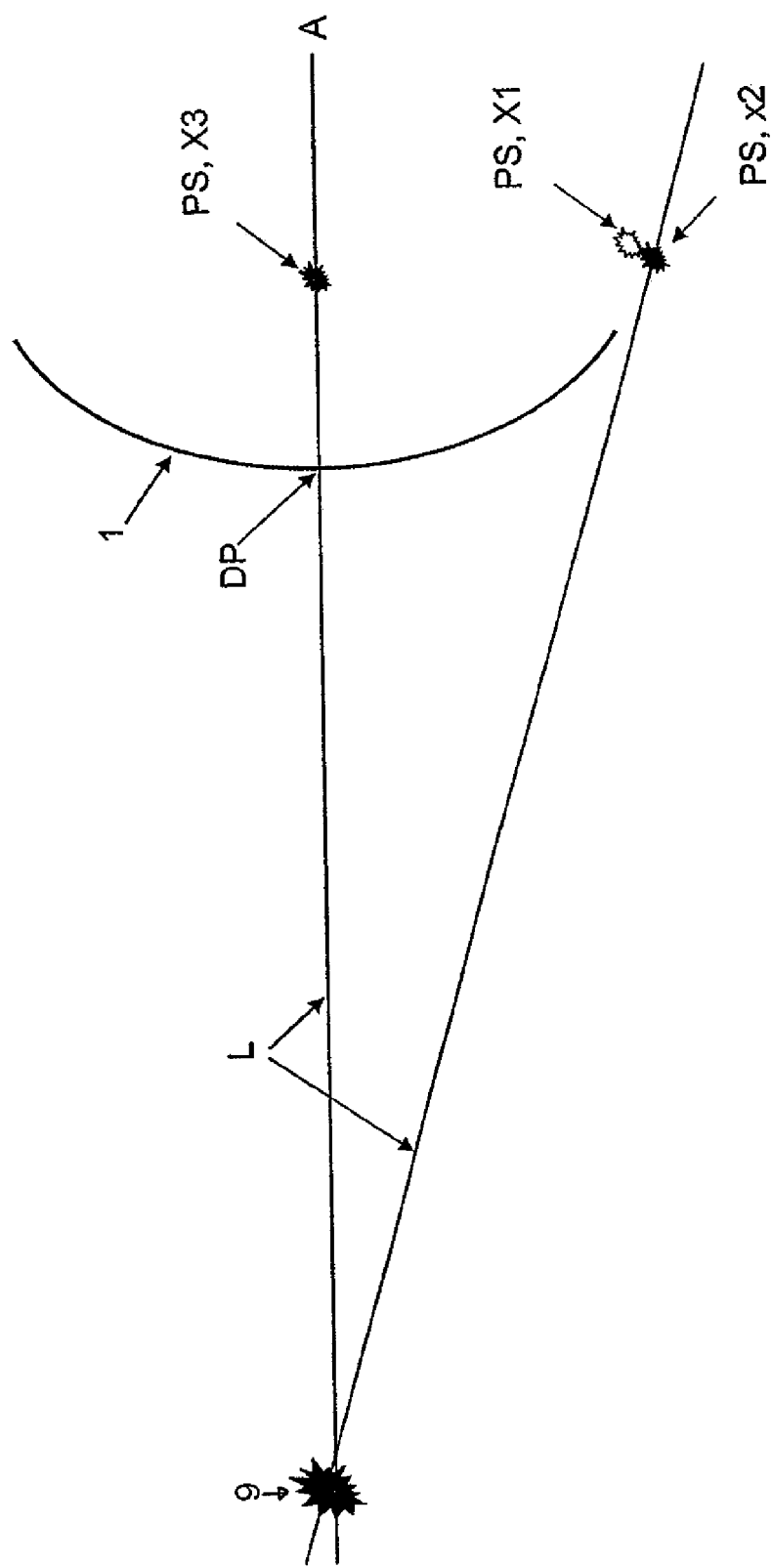
FIG. 5 shows an illustration of the location changeability of the virtual image.

At this point, an alternative possible occurrence of the scattered light event PS on the eye is noted only for reasons of completeness, which may also be assumed to be conceivable from the current understanding of the optical properties of the eye and changes nothing in the above considerations. For this purpose, reference is made to FIG. 4, which shows the beam geometry of an optical image of an object O on the cornea 1, which acts as a hollow mirror, and has a hollow mirror focal point B. The scattered light event PS occurring in the interior of the eye may be comprehended as an image of the light source by the optical hollow mirror effect and is used for exactly determining the optical axis A of the eye. A punctual light source 9 is used for this purpose as a fixation target (see FIG. 5), from which a parallel light beam bundle L originates and which is directed toward the eye 6 of the patient. In the case of the position x1 shown in FIG. 5, the scattered light event PS is located outside the optical axis A. The position x2 also lies outside the optical axis A, but x2 is to illustrate that the position x2 is assumed by the scattered light event PS when the eye has moved or shifted, that is, the position of the scattered light event PS has its position dependent on the eye of the patient in relation to the parallel light beam bundle L.

The penetration point DP of the optical axis A through the cornea is found exclusively in the case in which the scattered light event PS and the corneal reflection 1 are congruent along the parallel light beam bundle L. See position x3 of the scattered light event PS. In this case, parts of the parallel light beam bundle L are reflected back at the cornea surface into itself and the scattered light event PS is congruent with this reflection. This constellation is distinguished by a marked brightening of the reflection to be observed on the eye.

Figure 2:
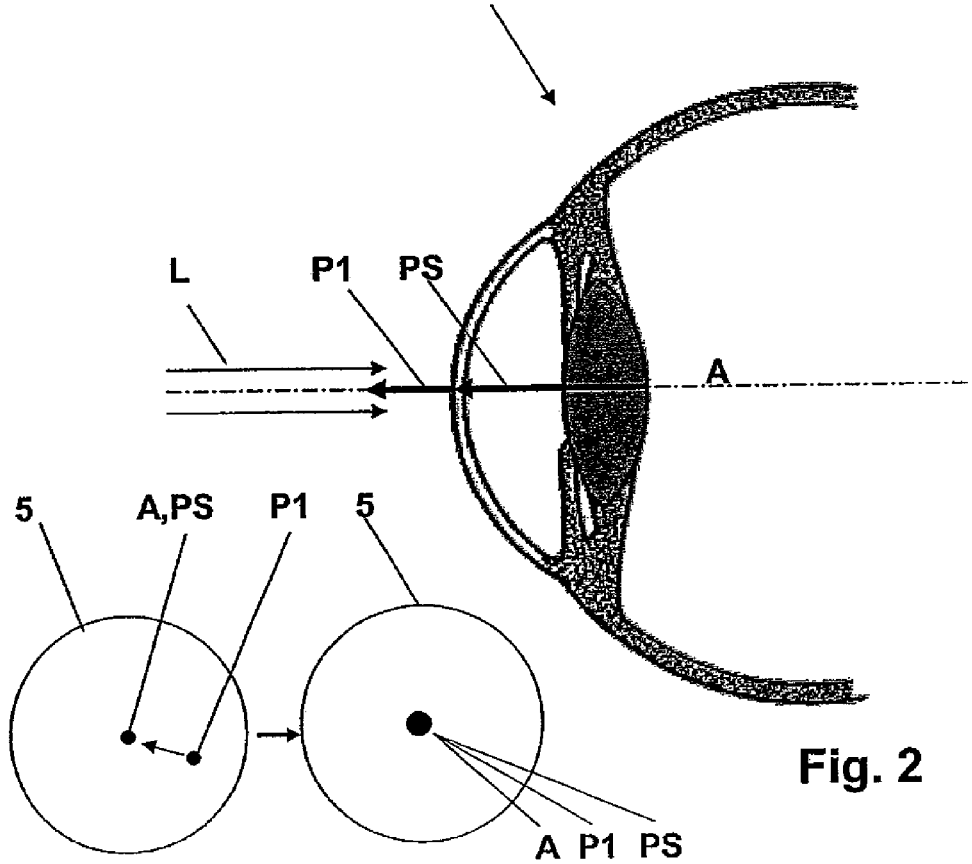
FIG. 2 shows an illumination situation having a centered optical axis.

The goal is thus to provide an illumination situation in which the parallel light beam bundle L incident on the eye 6 is oriented coaxially to the optical axis A. This is the case when the reflection event P1 and the scattered light event PS, as shown in the illustration of FIG. 2, are brought into congruency with one another. Two circular observation fields 5 are shown for better illustration in FIG. 2, which show the spatial positions of P1 and PS for an illumination of the eye using a parallel light beam path. The left observation field represents the image in which the optical axis A of the eye is maladjusted in relation to the parallel light beam path L. In this case, the spatial position of the reflection event on the cornea surface P1 deviates from the position of the scattered light event PS, which is already located along the optical axis A. To find the optical axis A which already runs through the scattered light event PS, the corneal reflection P1 in the beam direction of the parallel light beam bundle L illuminating the eye is to be brought into congruency with the scattered light event PS. This is shown in the right circular image illustration of FIG. 2. If both light events P1 and PS are congruent, their connecting axis is coincident with the visual or optical axis A of the eye, by which the spatial position of the eye is detected and fixed.

Figure 3:
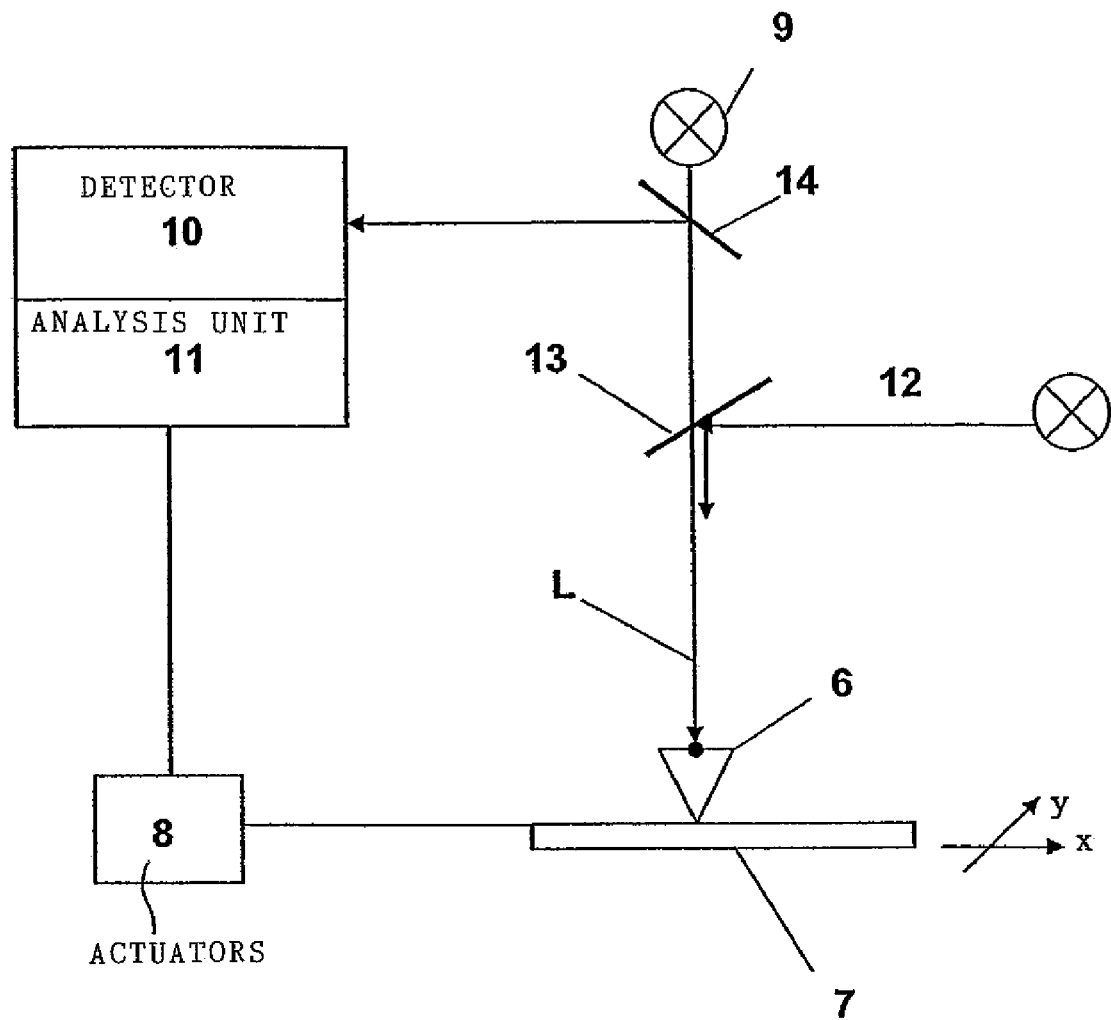
FIG. 3 shows a schematic illustration of the device for automatically finding the optical axis through an eye.

The device schematically illustrated in FIG. 3 is capable of automatically ascertaining the optical axis of the eye 6 and, in addition, tracking and/or fixing the detected optical axis of the eye 6 accordingly in relation to an optical reference system, for example, a treatment laser beam. For this purpose, the eye 6 to be treated of a subject (not shown further), who lies on a patient rest 7, which is movable in the x-y plane around at least two spatial axes via actuators 8 driven by motors, is positioned. A light source 9 emits a parallel light beam bundle L, which is directed into the pupil area of the eye 6, to generate the reflection and scattered light events on and in the eye 6 described above. The reflection and scattered light events occurring on or in the eye are imaged via an imaging object (not shown further) in a detector unit 10 via a deflection unit 14, in which the viewing fields 5 shown in FIG. 2 result. The detector unit 10 is preferably implemented as a video camera and is used for location-resolving position detection of the reflection and scattered light events imaged in the image plane of the video camera in regard to the Purkinje image P1 and the scattered light event PV, as explained above. Preferably, a separate imaging system and/or camera system may also be used in each case to detect the two light events, in order to sharply image both light events, which are possibly spaced apart from one another in depth.

The light events P1 and PS are to be brought in congruency in relation to the beam direction of the parallel light beam bundle L with the aid of a computer-supported graphic image analysis unit 11. For this purpose, a trajectory is ascertained, using which the light events P1 and PS, which initially are spatially separated, may be brought into congruency with one another. For this purpose, the analysis unit 11 generates control signals, which are transmitted to the adjustment unit 8, by which the patient rest is brought into a corresponding position. The procedure of bringing the two light events P1 and PS arising inside the eye 6 into congruency is performed completely automatically. As soon as the light events P1 and PS are congruent in the beam direction of the parallel light beam bundle L, their connecting axis defines the visual and/or optical axis of the eye 6. Further optical manipulations may be performed on the eye in precisely this configuration. For example, coupling a treatment laser beam 12 into the beam path of the parallel light beam bundle L with the aid of a semitransparent deflection mirror 13 is suitable. The treatment laser beam 12 is preferably used for performing photorefractive correction measures in or on the eye. If the position of the optical axis changes during the treatment in relation to the parallel light beam bundle and also to the treatment laser beam, a maladjustment is detected by the detector unit on the basis of the changing positions of the particular light events P1 and PS and corresponding correction control signals are generated under real-time conditions for readjustment of the eye.

The device according to the present invention schematically shown in FIG. 3 is thus used for finding the optical axis of an eye completely automatically and for its spatial fixation in the course of a regulated adjustment and/or tracking of the eye in relation to an optical reference system to perform photorefractive correction measures on the eye in particular.

LIST OF REFERENCE NUMERALS

1 cornea
2 aqueous humor
3 lens
4 vitreous humor
5 field of vision
6 eye
7 positioning region, patient rest
8 adjustment unit
9 light source
10 detector unit
11 analysis unit
12 treatment laser beam
13 deflection mirror
14 deflection mirror
L parallel light beam bundle
DP penetration point
A optical axis
B focal point of the cornea
PS scattered light event

The invention claimed is:

1. A device for detecting a spatial position of an optical axis of an eye of a human or animal subject and for centering a reference system in relation to the optical axis, including at least one light source emitting a parallel light beam bundle, a positioning region for the subject provided opposite the light source, means for the relative position orientation of the parallel light beam bundle in relation to the eye of the subject, and at least one detector unit for detecting reflection events caused in and on the eye by the parallel light beam bundle, wherein an analysis unit generates control signals on a basis of scattering and reflection events detected by the at least one detector unit, by which the means for relative position orientation are activated, the control signals being generated so that at least one reflection event and at least one scattered light event are to be brought into congruency in relation to a propagation direction of the parallel light beam bundle.

2. The device according to claim 1, wherein:
the eye has at least four optically active interfaces in the irradiation direction of the parallel light beam comprising air/cornea, cornea/aqueous humor, aqueous humor/lens, and lens/vitreous humor; and
the detector unit has at least one optical imaging system, by which a reflection event occurring in an area of the air/cornea interface, (the first Purkinje image), and a scattered light event occurring on the eye may be imaged sharply.

3. The device according to claim 2, wherein:
the detector unit provides at least one camera, including at least one field of vision directed to the pupil area of the eye and a position-resolving image plane for position detection of the reflection and/or scattered light events which may be imaged in the image plane of the video camera.

4. The device according to claim 2, wherein:
the means for relative position orientation of the parallel light beam bundle in relation to the eye of the patient includes at least one adjustment unit, by which the positioning region provided for the subject is movable in relation to the stationary light source in at least one plane.

5. The device according to one of claim 2, wherein:
the analysis unit provides a computer-supported graphic image analysis unit, which automatically detects at least the first Purkinje image and the scattered light event and calculates a trajectory to bring and keep two light events in congruency by relative position change between the light source and eye of the subject.

6. The device according to claim 2, comprising:
a further light source, whose light beam is selectively coupled into the parallel light beam directed onto the eye via at least one optical deflection element.

7. The device according to claim 1, wherein:
the detector unit provides at least one camera, including at least one field of vision directed to the pupil area of the eye and a position-resolving image plane for position detection of the reflection and/or scattered light events which may be imaged in the image plane of the video camera.

8. The device according to claim 7, wherein:
the means for relative position orientation of the parallel light beam bundle in relation to the eye of the patient includes at least one adjustment unit, by which the positioning region provided for the subject is movable in relation to the stationary light source in at least one plane.

9. The device according to one of claim 7, wherein:
the analysis unit provides a computer-supported graphic image analysis unit, which automatically detects at least the first Purkinje image and the scattered light event and calculates a trajectory to bring and keep two light events in congruency by relative position change between the light source and eye of the subject.

10. The device according to claim 1, wherein:
the means for relative position orientation of the parallel light beam bundle in relation to the eye of the patient includes at least one adjustment unit, by which the positioning region provided for the subject is movable in relation to the stationary light source in at least one plane.

11. The device according to one of claim 10, wherein:
the analysis unit provides a computer-supported graphic image analysis unit, which automatically detects at least the first Purkinje image and the scattered light event and calculates a trajectory to bring and keep two light events in congruency by relative position change between the light source and eye of the subject.

12. The device according to one of claim 1, wherein:
the analysis unit provides a computer-supported graphic image analysis unit, which automatically detects at least the first Purkinje image and the scattered light event and calculates a trajectory to bring and keep two light events in congruency by relative position change between the light source and eye of the subject.

13. The device according to claim 1, comprising:
a further light source, whose light beam is selectively coupled into the parallel light beam directed onto the eye via at least one optical deflection element.

14. The device according to claim 13, wherein:
the further light source is a treatment laser for targeted ablation and/or coagulation of tissue areas on or in the eye.

15. The device according to claim 13, wherein:
the light beam of the further light source and/or the parallel light beam bundle represents the reference system.

16. In a device detecting a spatial position of an optical axis of an eye of a human or animal subject and for centering a reference system in relation to the optical axis, including at least one light source emitting a parallel light beam bundle, a positioning region for the subject disposed opposite the light source, means for the relative position orientation of the parallel light beam bundle in relation to the eye of the subject, and at least one detector unit for detecting reflection events caused in and on the eye by the parallel light beam bundle, wherein an analysis unit generates control signals on a basis of scattering and reflection events detected by the at least one detector unit, by which the means for relative position orientation are activated, the control signals being generated so that at least one reflection event and at least one scattered light event are to be brought into congruency in relation to a propagation direction of the parallel light beam bundle, a method comprising:
detecting a penetration point of the optical axis of the eye through the cornea; and
automatically tracking an optical exposition in relation to the penetration point of the optical axis to the cornea.

17. The method according to claim 16, wherein:
the optical exposition is a therapeutic or diagnostic energy beam, or an optical axis of an imaging optic.

18. A method for detecting a spatial position of an optical axis of an eye of a human or animal subject and for centering a reference system in relation to the optical axis, in which the eye is illuminated using at least one parallel light beam bundle, the eye of the subject and/or the parallel light beam bundle are positioned in relation to one another so their positions may be changed and reflection events caused by the parallel light beam bundle on and/or inside the eye are detected using a detector unit, comprising:
detecting a reflection event caused by the parallel light beam bundle on the cornea surface and a scattered light event caused on the eye using the detector unit; and
changing the eye of the subject in its position in relation to the parallel light beam bundle so that the reflection event on the cornea surface and the scattered light event are brought into congruency along the parallel light beam bundle and held there.

19. The method according to claim 18, wherein:
for axial coincidence between a reflection event occurring on the cornea surface and a scattered light event, a reflection position connected to the reflection event is determined as a penetration point of the optical axis of the eye through the cornea.

20. The method according to claim 19, wherein:
a spatial position of the penetration point is stored.

* * * * *